US008580857B2

(12) United States Patent
Au et al.

(10) Patent No.: US 8,580,857 B2
(45) Date of Patent: Nov. 12, 2013

(54) METHODS AND COMPOSITIONS TO DETERMINE THE CHEMOSENSITIZING DOSE OF SURAMIN USED IN COMBINATION THERAPY

(76) Inventors: Jessie L. -S. Au, Columbus, OH (US); M. Guillaume Wientjes, Columbus, OH (US)

( * ) Notice: Subject to any disclaimer, the term of this patent is extended or adjusted under 35 U.S.C. 154(b) by 0 days.

(21) Appl. No.: 13/031,306

(22) Filed: Feb. 21, 2011

(65) Prior Publication Data

US 2011/0142794 A1 Jun. 16, 2011

Related U.S. Application Data

(60) Division of application No. 10/807,620, filed on Mar. 24, 2004, now abandoned, which is a continuation-in-part of application No. PCT/US02/30210, filed on Sep. 24, 2002.

(60) Provisional application No. 60/324,704, filed on Sep. 24, 2001.

(51) Int. Cl.
*A61K 31/17* (2006.01)

(52) U.S. Cl.
USPC .................................................. 514/597

(58) Field of Classification Search
None
See application file for complete search history.

(56) References Cited

U.S. PATENT DOCUMENTS 5,597,830 A * 1/1997 Klohs et al. .................. 514/283

OTHER PUBLICATIONS

Tu et al. Clinical Cancer Research, May 1998, vol. 4, pp. 1193-1201.*
Falcone et al. Tumori, 1998, vol. 84, No. 6, pp. 666-668 (Abstract attached).*
Calvert, AH, Newell, DR, Gumbrell, LA et al., Carboplatin dosage: prospective evaluation of a simple formula based on renal function. J. Clin. Oncol., yr 1989, pp. 1748-1756, vol. 7.
Chen, D, Song, SH, Wientjes, MG et al., Nontoxic suramin as a chemosensitizer in patients: dosing nomogram development. Pharm. Res., yr 2006, pp. 1265-1274, vol. 23.
Collins, JM, Klecker, RW, Jr., Yarchoan, R et al., Clinical pharmacokinetics of suramin in patients with HTLV-III/LAV infection. J. Clin. Pharmacol., yr 1986, pp. 22-26, vol. 26.
Motzer, RJ, Nanus, DM, O'Moore, P et al., Phase II trial of suramin in patients with advanced renal cell carcinoma: treatment results, pharmacokinetics, and tumor growth factor expression. Cancer Res., yr 1992, pp. 5775-5779, vol. 52.
Piscitelli, SC, Forrest, A, Lush, RM et al., Pharmacometric analysis of the effect of furosemide on suramin pharmacokinetics. Pharmacotherapy, yr 1997, pp. 431-437, vol. 17.
Warner-Lambert Co. Warner Lambert 10K report to Securities and Exchange Committee. Dec. 31, 1999.

* cited by examiner

*Primary Examiner* — James D Anderson
(74) *Attorney, Agent, or Firm* — Mueller Law, LLC; Jerry K. Mueller, Jr.

(57) ABSTRACT

A method for determining a therapeutically effective amount of suramin for administering to a patient, who is to receive a cytotoxic agent, which comprises the steps of determining the circulating suramin concentration in the patient; administering suramin, if required, to establish a low circulating concentration of suramin in the patient of below about 200 μM; and administering the chemotherapeutic agent to the patient when the low circulating concentration of suramin is present in the patient. Conveniently a nomogram can be constructed for use in clinical settings with the suramin.

18 Claims, 1 Drawing Sheet

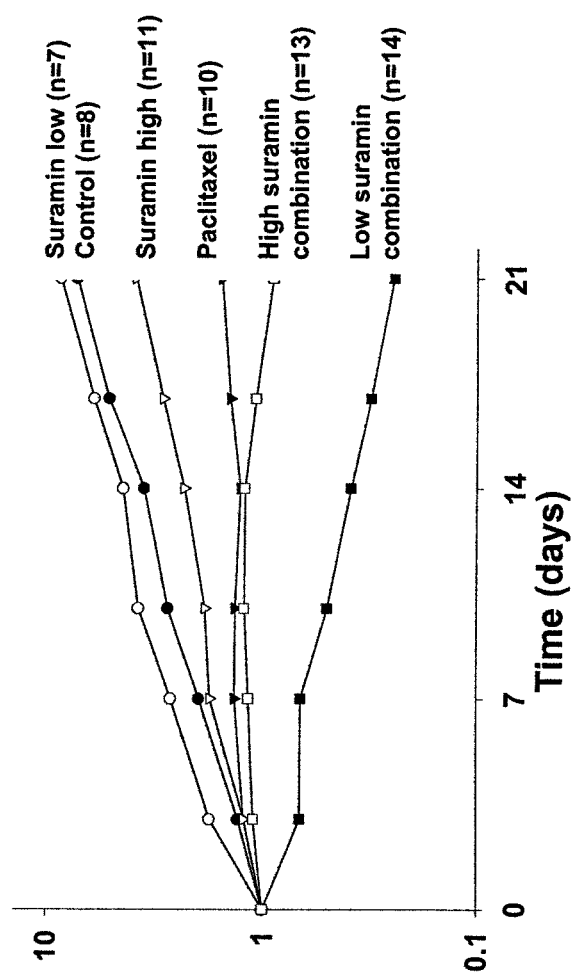

METHODS AND COMPOSITIONS TO DETERMINE THE CHEMOSENSITIZING DOSE OF SURAMIN USED IN COMBINATION THERAPY

CROSS-REFERENCE TO RELATED APPLICATIONS

This application is a divisional of application serial number 10/807,620, filed Mar. 24, 2004, now abandoned which is a continuation-in-part, of application serial number PCT/US02/30210, filed Sep. 24, 2002; which claims priority to U.S. Provisional Application No., 60/324,704, entitled "Methods and Compositions for Modulating Cell Proliferation and Cell Death" filed on Sep. 24, 2001. The contents of the patents, patent applications, and references cited throughout this specification are hereby incorporated by reference in their entireties.

GOVERNMENT SPONSORED RESEARCH

This work was supported, in part, by grants from the National Cancer Institute, National Institutes of Health, and Department of Health and Human Services (Grant Numbers R37CA49816; RO1CA78577; RO1CA74179; and UO1CA76576).

BACKGROUND OF THE INVENTION

1. Field of the Invention

The present invention relates to a method to determine the dose requirements of suramin used as a chemosensitizer to enhance the efficacy of other chemotherapeutic agents.

2. Description of the Prior Art

Suramin is an anticancer agent with modest activity in single agent therapy. A large number of previous studies have evaluated suramin in high-dose regimens, either as single agent or in combination with other chemotherapeutics. These studies, which aimed to achieve plasma concentrations between 150 and 300 µg/ml or about 100 to 200 µM, showed a modest activity of high-dose suramin for single agent therapy, in the face of extensive drug toxicity. (Eisenberger, et al (1995) *J Clin Oncol* 13:2174-2186). A typical suramin dosing schedule aimed at maintaining suramin plasma concentrations between 100 and 200 µg/ml consists of an initial administration of 2100 mg/m$^2$ in the first week with the subsequent doses repeated every 28 days for 6 months or longer; the subsequent doses are adjusted using the Bayesian pharmacokinetic method (Dawson, et al (1998) *Clin Cancer Res* 4:37-44, Falcone, et al (1999) *Cancer* 86:470-476). Moreover, the methods of the art for using suramin in combination with other cytotoxic agents often administer high doses of suramin at a more frequent schedule or a longer duration compared to the frequency and the treatment duration for the other cytotoxic agents. For example, in the combination of suramin and doxorubicin for the treatment of androgen-independent prostate cancer, the duration of doxorubicin treatment was up to 20 weeks, whereas the duration of the suramin treatment was up to 45 weeks (Tu, et al (1998) *Clin Cancer Res* 4:1193-1201). For example, in the combination of suramin and mitomycin C for the treatment of hormone-resistant prostate cancer, suramin was given weekly whereas mitomycin C was given only every 5 weeks (Rapoport, et al (1993) *Ann Oncol* 4:567-573). At these doses and chronic treatments, suramin causes the following toxicity in a human patient: adrenal insufficiency, coagulopathy, peripheral neuropathy, and proximal muscle weakness (Dorr and Von Hoff, *Cancer Chemotherapy Handbook,* 1994, pp 859-866). To overcome the adrenolytic toxicity, patients on high-dose suramin regimens were co-administered replacement steroid treatments (Dorr and Von Hoff, id).

Combination regimens of suramin, at doses that result in relatively constant plasma concentrations of between about 100 to about 200 µM over several months, and other chemotherapeutic agents have shown either limited benefit or have resulted in toxicity that does not encourage further evaluation of these regimens (e.g., Miglietta, et al., *J. Cancer Res. Clini. Oncol.* 23:407-410, 1997; Falcone A, et al. *Tumori* 84:666, 1998; Falcone A, et al. *Cancer* 86:470, 1999; Rapoport B, et al. *Ann Oncol* 4:567, 1993).

The lack of synergistic interaction between suramin, at plasma concentrations between about 100 to about 200 µM maintained for several months, and other chemotherapeutic agents may be a result of the cell cycle perturbation caused by suramin; suramin at constant concentrations of above 50 µM maintained for at least one or two days has been shown to induce cell cycle arrest with accumulation of cells at different phases of the cell cycle and may therefore interfere with the activity of other chemotherapeutic agents that act on other phases of the cell cycle, as well as interfere with the activity of other chemotherapeutic agents whose activity depends on the ability of cells to progress through the cell cycle (Qiao L, et al. *Biochem Biophys Res Commun* 201:581, 1994; Howard S, et al. *Clin Cancer Res* 2:269, 1996; Palayoor S T, et al., *Radiat Res,* 148:105-114, 1997).

Applicants have disclosed in a previous patent application (PCT/US00/40103) that acidic and basic fibroblast growth factors (aFGF and bFGF) present in tumor tissues induce resistance of tumor cells to chemotherapy, and that this FGF-mediated resistance can be overcome by low concentrations of suramin of less than about 50 µM. However, it is not known whether the chemosensitizing effect of suramin would be diminished at higher doses delivering higher plasma concentrations in vivo.

The present invention shows that only low doses of suramin, which yielded between about 10 to about 50 µM plasma concentrations over the duration (e.g., 6 hours) when a chemotherapeutic agent (e.g., paclitaxel) was present in the plasma at therapeutically significant levels, enhanced the efficacy of chemotherapy in tumor-bearing animals. In contrast, high doses of suramin, that yielded concentrations between about 300 to about 650 µM over about the same duration, did not enhance the efficacy and only enhanced the toxicity of chemotherapy. Similarly, Applicants disclose the results of a Phase I trial, showing that addition of low dose suramin, that yielded between about 10 to about 50 µM plasma concentrations, over the duration when other chemotherapeutic agents (i.e., paclitaxel and carboplatin) were present at therapeutically significant levels, enhanced the response of cancer patients to a standard therapy of paclitaxel plus carboplatin. These findings are surprising in view of the prior art teaching that suramin does not improve the efficacy of other chemotherapeutic agents in human patients (Miglietta, et al, Falcone A, et al., 1998; Falcone A, et al., 1999; Rapoport, et al., 1993). These findings also are highly counter-intuitive, as it is generally believed that administration of a higher drug dose yields a greater effect rather than a lower effect, as compared to a lower dose. Furthermore, the low-dose suramin treatment did not induce adrenal insufficiency and, accordingly, replacement steroid therapy was not necessary in patients receiving low-dose suramin.

Previous studies to guide the dose selection of patients treated with high-dose suramin have used a Bayesian pharmacokinetic method, entailing continuous suramin pharmacokinetic monitoring that requires measurement of actual plasma concentrations in each patient over several months. This earlier approach is a highly labor-intensive and costly procedure that can only be performed in a limited number of clinical centers (Reyno L M, et al. *J Clin Oncol* 13:2187-2195, 1995), and, therefore, has limited applicability.

The application of population pharmacokinetics permitted the development of more easily applied fixed dosing schedules (Reyno L M, et al. *J Clin Oncol* 13:2187-2195, 1995; Small E, et al. *J Clin Oncol* 18:1440-1450, 2000). These schedules used the same initial dose on a per body surface area basis for all patients. Subsequent doses were reduced according to predetermined schedules. These regimens were designed to maintain constant and high plasma concentrations in the range of 100 to 200 μM, over long treatment durations of more than two months. In addition, these studies were limited to male patients with prostate cancer. Consequently, these regimens could not be applied to the use of suramin in combination therapy as a chemosensitizer in both male and female patients. As a chemosensitizer, the plasma concentrations of suramin are maintained at a narrow range of much lower levels (e.g., between about 10 to about 50 μM, e.g., below 300 to 650 μM), and only transiently while other chemotherapeutic agents are present at therapeutically significant concentrations (e.g., less than one week).

The fixed dosing schedules described in the prior art (Reyno, et al, Small E, et al) also do not offer provisions for deviation from the planned treatment schedule. However, in clinical practice, treatment delay due to toxicity or scheduling conflicts is very common. This, in turn, makes the fixed dosing schedules an impractical approach for administering suramin.

Further, the invention discloses a 180% inter-subject variability in suramin disposition in cancer patients, in part due to slower drug elimination in female patients compared to male patients. This gender-related difference in suramin elimination has not been previously demonstrated. The large inter-subject variability indicates that administering the same dose of suramin will not result in the same, desired plasma concentrations in all patients.

Accordingly, the methods described in the prior art for calculating the dose of suramin used as a cytotoxic agent cannot be used for calculating the suramin dose used as a chemosensitizer.

The invention discloses a simple and practical method to calculate a suramin dose in individual patients, based on the target chemosensitizing suramin concentrations and duration of suramin exposure (e.g., plasma concentrations of between about 10 to about 50 μM maintained over 48 hours), and demographic characteristics of a patient including, but not limited to, the squared value of the body surface area and gender of a patient, and the duration between treatments. This new method, therefore, can be used to calculate the suramin dose for use as a chemosensitizer, in both male and female patients, and can accommodate delay in treatments.

For other drugs where the maintenance of a narrow range of exposure is required, various other methods have been devised. For example, for the administration of carboplatin, a narrow range of integrated product of concentration and time (area under the concentration-time curve) is desired, and the carboplatin dose is calculated based on a patient's creatinine clearance (Calvert, et al, *J. Clin. Onc.* 7:1748, 1989). There is no disclosure, however, of a method to calculate the dose requirements for low-dose suramin that produces chemosensitization.

SUMMARY OF THE INVENTION

The invention is based, at least in part, on the following discoveries by the inventors.

Administration of suramin, in combination with other chemotherapeutic agents, to a subject at different dosages yielding different plasma concentrations, can result in opposite effects. Administration of low doses of suramin, which yields plasma concentrations of between about 10 to about 50 μM over the duration when other chemotherapeutic agents are present in the plasma at therapeutically significant levels, enhances the efficacy without potentiating the toxicity of co-administered chemotherapeutic agents. On the contrary, administration of high doses of suramin, which yields between 300 to 650 μM over the same time period, does not enhance the efficacy, but potentiate the toxicity of co-administered chemotherapeutic agents. Hence, the chemosensitizing effect of suramin is highly dose-dependent and concentration-dependent, and occurs at a concentration range of between about 10 to about 50 μM and below about 300 to about 650 μM maintained over the duration when the co-administered chemotherapeutic agent is present at therapeutically significant levels.

Applicants also tested in cancer patients the use of low doses of suramin selected to deliver plasma concentrations in the range known to produce chemosensitization in tumor-bearing animals, over the duration when other chemotherapeutic agents (i.e., paclitaxel and carboplatin) were present in the plasma at therapeutically significant levels (e.g., about 10 to about 50 μM suramin concentrations over 48 hours). The results indicate that addition of low doses of suramin enhanced the efficacy of chemotherapy in cancer patients.

Applicants further found that the elimination of suramin, at the low dose that yielded between about 10 to about 50 μM over 48 hours produces chemosensitization, is more rapid and shows more inter-subject variability in human cancer patients, compared to the results shown in the prior art when suramin was given at high doses that yielded between about 100 to about 200 μM plasma concentrations in patients.

These above findings, collectively, indicate the importance and the need of a method of determining the dose and treatment schedules of suramin to be used as a chemosensitizer.

Applicants further discovered that the pharmacokinetics of low-dose suramin depends on, and can be predicted from, patient characteristics. The invention discloses a method for calculating, for individual patients, the suramin dose that would yield the desired plasma suramin concentrations known to produce chemosensitization. The invention further discloses a method to prepare nomograms and discloses nomograms for calculating the suramin dose in individual patients.

Other features and advantages of the invention will be apparent from the following detailed description, and from the claims.

BRIEF DESCRIPTION OF THE DRAWING

FIG. 1 graphically depicts the effect of suramin dose on chemosensitization. Immunodeficient mice bearing well-established subcutaneous human prostate PC3 xenograft tumors were treated with saline (controls), a chemotherapeutic agent (i.e., paclitaxel), low dose suramin, high dose suramin, a combination of paclitaxel plus low dose suramin, or a combination of paclitaxel plus high dose suramin. The dose of paclitaxel was 15 mg/kg and was given twice weekly for three weeks. Two doses of suramin were used. The low suramin dose was 10 mg/kg and was given twice weekly for three weeks. The high suramin dose group received a loading dose of 200 mg/kg, followed by 5 doses of 130 mg/kg each, over three weeks. Example 1 further expounds on FIG. 1.

DETAILED DESCRIPTION OF THE INVENTION

Before further description of the invention, certain terms employed in the specification, examples and appended claims are, for convenience, collected here.

Definitions

As used herein, the terms "cytotoxic agent", "chemotherapeutic agent", "anticancer agent", and "antitumor agent" are used interchangeably herein and refer to agents that have the property of inhibiting the growth or proliferation (e.g., a cytostatic agent), or inducing the killing, of hyperproliferative cells.

As used herein, a "therapeutically effective amount" of suramin refers to an amount of suramin that is effective, upon single- or multiple-dose administration to the subject, e.g., a patient, at inhibiting the growth or proliferation, or inducing the killing, of hyperproliferative cells, e.g., cancer cells. The term "therapeutically effective amount" also refers to an amount of suramin that is administered, e.g., coadministered, (i.e., sequentially or concomitantly) with one or more cytotoxic agents such that suramin and the cytotoxic agent, are effective, upon single- or multiple-dose administration to the subject, e.g., a patient, at inhibiting the growth or proliferation, or inducing the killing, of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

As used herein, "chemosensitization" and "chemosensitizing effect" are used interchangeably and refer to the enhancement of chemotherapy efficacy by suramin. "Chemosensitizer" refers to the agent, e.g., suramin, that enhances the efficacy of another agent.

As used herein, "high dose suramin" and "high dose(s) of suramin" are used interchangeably and refer to suramin used as a cytotoxic agent and at doses that when injected into a subject, result in a plasma concentration range of between about 300 to about 650 µM maintained for about six to eight hours, or result in a plasma concentration range of between 100 to 200 µM maintained for more than one or two months.

As used herein, "low dose suramin" refers to suramin used as a chemosensitizer and at doses that when injected into a subject, result in a plasma concentration range of below about 300 to about 650 µM maintained for about six to eight hours, or result in a plasma concentration range of between 100 to 200 µM maintained for more than one or two months.

As used herein, "high dose suramin regimen" refers to a treatment that administers a high dose of suramin to a subject.

As used herein, "low dose suramin regimen" refers to a treatment that administers a low dose of suramin to a subject.

As used herein, "duration when the co-administered chemotherapeutic agent(s) are present at therapeutically significant concentrations or levels" refers to the time period when the co-administered chemotherapeutic agent is present or detectable in the circulating blood or plasma, or the duration over which the exposure to the co-administered chemotherapeutic agent accounts for about 90% of the total exposure to the co-administered agent, e.g., measured as area-under-concentration-time-curve, or the duration which is approximately equal to three to four terminal half-lives of the co-administered chemotherapeutic agent.

As used herein, "covariates" refers to physiological or pathological parameters of patients that may contribute to the inter-subject variability in the elimination of low dose suramin.

As used herein, "PBPK" refers to population-based pharmacokinetic analysis, and "PBPK-based dosing method" refers to a method developed using PBPK to determine the suramin dosing regimens that produce chemosensitization. This method is detailed in EXAMPLE IV.

As used herein, "a nomogram" refers to a tabulation and/or predictive formula(ae) which allow for the determination of a therapeutically effective amount(s) of an agent for administering to a subject, e.g., a human patient, based on one or more readily obtained parameters, including, but not limited to, the patient's gender, age, body weight or body surface area, or the time lapsed since the previous drug treatment.

As used herein, other terms such as "coadministration", "an effective amount of suramin and a cytotoxic agent", "subject", "human", "non-human", "inhibiting the growth or proliferation of the hyperproliferative cell", "inducing the killing of the hyperproliferative cell", "induce", "inhibit", "potentiate", "elevate", "increase", "decrease", "hyperproliferative", "hyperplastic", "malignant", "neoplastic", "pathologic hyperproliferative", "neoplasia", "hyperplasia", "tumors", "carcinoma", "adenocarcinoma", "sarcoma", "leukemia", "leukemic cancer" "myelomas", and "lymphomas" are as described in the earlier patent application No. PCT/US00/40103.

CONTINUED DETAILED DESCRIPTION OF INVENTION

In one aspect, the invention features the use of low dose suramin as a chemosensitizer, in combination with at least one other chemotherapeutic agent.

In a preferred embodiment, low dose suramin is administered, in combination with at least one other chemotherapeutic agent, to a subject.

In a preferred embodiment, low dose suramin is co-administered with the same, or a different chemotherapeutic agent, to a subject.

In a preferred embodiment, low dose suramin is co-administered with repeated dosages of the same, or a different chemotherapeutic agent, to a subject.

In a preferred embodiment, the dosing schedule of low dose suramin yields plasma concentrations of suramin, preferably below the range of between about 300 to about 600 µM, preferably below the range of between about 150 to about 200 µM, advantageously below the range of between about 135 to about 200 µM, more advantageously below the range of between about 120 to about 200 µM, preferably below the range of between about 105 to about 200 µM, more preferably below the range of between about 90 to about 200 µM, more preferably below the range of between about 75 to about 200 µM, more preferably below the range of between about 60 to about 200 µM, and even more preferably at the range of between about 10 to about 50 µM, over the duration when a co-administered chemotherapeutic agent is present in the subject at therapeutically significant levels.

In a preferred embodiment, a chemotherapeutic agent is given repeatedly for multiple treatment cycles scheduled at time intervals of approximately three weeks.

In another embodiment, a chemotherapeutic agent is given repeatedly for multiple treatment cycles scheduled at time intervals of approximately one week.

In a preferred embodiment, the dosing regimens of chemotherapy include administration of multiple treatment cycles administered at irregular time intervals.

In a preferred embodiment, low dose suramin is given repeatedly for multiple treatment cycles scheduled at time intervals of approximately three weeks.

In another embodiment, low dose suramin is given repeatedly for multiple treatment cycles scheduled at time intervals of approximately one week.

In a preferred embodiment, the dosing regimen of low dose suramin includes administration of multiple treatment cycles scheduled at irregular time intervals.

In a preferred embodiment, the dosing regimen of low dose suramin includes repeated dosages of suramin within a single treatment cycle.

In a preferred embodiment, combination therapy of low dose suramin and at least one other chemotherapeutic agent inhibits the proliferation of, or enhances the killing of, a hyperproliferative cell derived from malignant or benign tumors, or from a benign hyperplastic growth.

In another embodiment, low dose suramin is administered in combination therapy with at least one other chemotherapeutic agent to human patients.

In another embodiment, low dose suramin is administered in combination therapy with at least one other chemotherapeutic agent to non-human mammals.

In a preferred embodiment, low dose suramin enhances the efficacy of the chemotherapeutic agent, e.g., a cytotoxic agent, relative to the effect of the cytotoxic agent in the absence of low dose suramin.

In a preferred embodiment, low dose suramin is administered with at least one chemotherapeutic agent, so as to inhibit the proliferation of, or to enhance the killing of, a hyperproliferative cell derived from malignant or benign tumors.

In one embodiment, suramin is administered with at least one cytotoxic agent. The enhanced, and sometimes synergistic, effect of suramin with at least one anticancer agent, in addition to improving the efficacy of these anticancer agents, may allow for the administration of lower doses of these anticancer agents, thus reducing the induction of side effects in a subject, (e.g., a patient). For example, the subject is a patient with non-small cell lung cancer, who is treated with a combination of paclitaxel, carboplatin, and suramin.

In another aspect, the invention teaches not to use high dose suramin, in combination with other chemotherapeutic agents.

In a preferred embodiment, high doses of suramin (i.e., above about 200 to 300 µM) can be administered to a subject; however, administration of a chemotherapeutic agent is delayed until the plasma concentrations of suramin have decreased to between the range of about 10 to 50 µM, during which time the chemotherapeutic agent is administered.

In another aspect, the invention features a method of identifying the dose of suramin to be used as a chemosensitizer, in combination with an agent, e.g., a cytotoxic agent, in a subject. The method is comprised of the steps of:
(a) implanting animals,
(b) administering suramin and at least one other chemotherapeutic agent to tumor-bearing animals,
(c) fixing the dose of the other chemotherapeutic agent such that this dose results in tumor growth delay or tumor size reduction,
(d) varying the dose of suramin and monitoring the size of the animal tumors over time,
(e) measuring the plasma concentrations of suramin derived from suramin doses that produce chemosensitization, and
(f) measuring the plasma concentrations of suramin derived from suramin doses that do not produce chemosensitization.

In a preferred embodiment, the invention features a method for determining, for a chemotherapeutic agent, the extent of enhancement of therapeutic efficacy that is obtained by chemosensitization with low dose suramin, in order to identify the chemotherapeutic agent that, when co-administered with low dose suramin to a subject, will produce the desired enhanced efficacy by suramin.

In another aspect, the invention features a method for determining a therapeutically effective amount of suramin as a chemosensitizer for administering to a patient. The method is comprised of the steps of:
  determining the gender and the squared value of the body surface area of a patient,
  determining the time elapsed, in days, since the initiation of the last suramin treatment, and
  calculating the dose of low dose suramin using a nomogram that shows the dose according to the above three parameters, such that a therapeutic effective amount of suramin is predicted by the nomogram (e.g., as set forth in Table 7).

In another aspect, the invention features a method to derive the equations and to obtain the values of population-average pharmacokinetic parameters of low dose suramin. These equation and parameters are used for determining a therapeutically effective amount of low dose suramin used as a chemosensitizer for administering to a patient. The method is detailed in Example IV and is comprised of the steps of:
(a) determining the pharmacokinetics of low dose suramin in subjects,
(b) defining the inter-subject variability of pharmacokinetic parameters,
(c) defining the sources of inter-subject variability of pharmacokinetic parameters using population-based pharmacokinetic analysis,
(d) establishing the population models that describe, for the overall population of patients that receive low dose suramin, the mathematical relationships between the total body clearance of suramin and relevant physiological or pathological parameters of patients, and between the volume of distribution of suramin and relevant physiological or pathological parameters of patients,
(e) using the established population models to calculate the dose of low dose suramin for individual patients, based on the desired target drug concentrations at the target time points and the characteristic of an individual patient (e.g., gender, squared value of body surface area), and
(f) verifying the established population models in a prospective study.

Exemplary tumors are as described in an earlier patent application No. PCT/US00/40103. Examples of diagnosis of an established tumor also are as described in the earlier application PCT/US00/40103.

Exemplary benign hyperplastic growths are as described in the earlier application PCT/US00/40103.

In a preferred embodiment, suramin is administered in combination with at least one cytotoxic agent. The term "in combination" in this context means that the agents are given substantially contemporaneously, either simultaneously or sequentially. If given sequentially, at the onset of administration of the second compound, the first of the two compounds is preferably still detectable at effective concentrations at the site where treatment effect is desired.

For example, low dose suramin can be used in combination therapy with conventional cancer chemotherapeutics. Conventional treatment regimens for tumors include radiation, antitumor agents, interferons, interleukins, tumor necrosis factors, or a combination of two or more of these agents.

The cytotoxic agents include, but are not limited to, an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, and/or radiation.

Exemplary cytotoxic agents include, but are not limited to, paclitaxel, vincristine, vinblastine, vindesine, vinorelbin, docetaxel, topotecan, camptothecin, irinotecan hydrochloride, doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytosine arabinoside, trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside, cladribine, ftorafur, UFT (combination of uracil and ftorafur), 5-fluoro-2'-deoxyuridine, 5'-deoxy-5-fluorouridine, tiazofurin, Xeloda (Capecitabine), cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycins, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, Herceptin, anti-CD20 (Rituxan), C225, Iressa, alpha, interferon beta, interferon gamma, interleukin 2, interleukin 4, interleukin 12, tumor necrosis factors, and radiation.

Examples of additional agents that can be used in combination with low dose suramin include, but are not limited to, hydroxyurea, azathioprine, aminopterin, trimethoprin, pyrimethamine, pyritrexim, DDMP (2,4 diamino-5(3',4' dichlorophenyl)6 methylpyrimidine), 5,10-dideazatetrahydrofolate,10-propargyl-5,8 dideazafolate (CB3717), 10-ethyl-10-deaza-aminopterin, deoxycytidine, 5-aza-cytosine arabinoside, N-4-palmitoyl-ara C, 2'-azido-2'-deoxy-ara C, N4-behenoyl-ara C, CCNU (lomustine), estramustine, MeCCNU, triethylene melamine, trenimon, dimethyl busulfan, streptozotocin, chlorozotocin, procarbazine, hexamethylmelamine (Altretamine), pentamethylmelamine (PMM), tetraplatin, oxaliplatin, platinum-DACH, aziridinylbenzoquinone (AZQ), bleomycin, tallysomycin $S_{10}^{b}$, liblomycin, pepleomycin, asparaginase (Elspar), pegaspargase (Oncaspar), Cladrabine (leustatin), porfimer sodium (Photofrin), amonofide, deoxyspergualin, dihydrolenperone, flavone acetic acid, gallium nitrate, and hexamethylene bisacetamine (HMBA).

EXAMPLES

The invention now being generally described, it will be more readily understood by reference to the following examples, which are included merely for purposes of illustration of certain aspects and embodiments of the present invention, and are not intended to limit the invention.

Example I

Low Dose, but not High Dose, Suramin Enhances the In Vivo Antitumor Activity of Chemotherapy This example describes the importance of administering therapeutically effective amounts of suramin as a chemosensitizer for, e.g., enhancing chemotherapy efficacy.

A study was conducted to evaluate the effect of the dose size of suramin on its ability to enhance the antitumor activity of chemotherapy. The relevant tumor model used was human prostate PC3 xenograft implanted subcutaneously in immunodeficient mice. Drug treatment was initiated after tumors were palpable and greater than 3 mm in diameter. The dose of paclitaxel was 15 mg/kg and was given twice weekly for three weeks. Two doses of suramin were used. The low suramin dose was 10 mg/kg and was given twice weekly for three weeks (referred to as low dose suramin regimen). Animals in the high suramin dose group received a loading dose of 200 mg/kg, followed by 5 doses of 130 mg/kg each, over three weeks (referred to as high dose suramin regimen). Animals received saline, paclitaxel alone, low dose suramin alone, high dose suramin alone, or a combination of the two drugs, and the results of these studies are shown in FIG. 1.

In test animals in the saline and low dose suramin groups, the tumor size increased with time, reaching the highest levels of about 800% of the initial tumor size. The high dose suramin group showed a slower tumor growth, indicating that high dose suramin produced antitumor activity. However, the difference in the tumor size between the high dose suramin group and the control group was not significant ($p>0.05$). Paclitaxel alone suppressed tumor growth; the difference in the tumor size between this group and the control group was significant ($p<0.05$). The combination of paclitaxel and high dose suramin showed similar effect as paclitaxel alone. In contrast, the combination of paclitaxel and low dose suramin showed significantly enhanced antitumor effect compared to paclitaxel alone ($p<0.05$). Moreover, this is the only group that showed significant reduction in tumor size to about 20% of the initial size.

Because a post-treatment residual tumor consisted of apoptotic and non-apoptotic cells, the effects of different treatments on the fractions of non-apoptotic (and therefore not committed to death) and apoptotic (dead or committed) cells were evaluated. Briefly, residual tumors were removed from animals after termination of treatment, and histologic tumor sections were prepared. Tumor sections were examined microscopically under 400× magnification. For each tumor, at least 4 sections were evaluated. Apoptotic cells were identified by their characteristic morphologies, i.e., presence of apoptotic bodies, condensed nuclei and fragmented nuclei. The results are shown in Table 1. The control group showed the highest number of residual tumor cells and the highest number of non-apoptotic cells, per 400× field. The low dose suramin group showed a slightly lower number of non-apoptotic cells, but the difference between this group and the control was not significant ($p>0.05$). Compared to the control group, the high dose suramin group, and the paclitaxel group, the two combination groups showed significantly lower numbers of non-apoptotic cells ($p<0.05$ for all four groups).

A comparison of the paclitaxel group and the paclitaxel/high dose suramin combination group shows similar numbers of non-apoptotic and apoptotic cells in the two groups ($p>0.05$), indicating that the addition of high dose suramin did not significantly alter the antitumor activity of paclitaxel. However, the paclitaxel/low dose suramin combination group showed 7-fold fewer non-apoptotic cells compared to the paclitaxel group, indicating that the addition of low dose significantly enhanced the antitumor activity of paclitaxel (p<0.05).

TABLE 1

Effect of chemotherapy and different suramin doses on non-apoptotic and apoptotic cells in tumors and body weight. Data are mean ± SD

|  | Control | Low dose suramin | High dose suramin | Paclitaxel | Paclitaxel + low suramin | Paclitaxel + high suramin |
|---|---|---|---|---|---|---|
| | | | Number of cells in a 400x field | | | |
| Non-apoptotic | 76 ± 38 | 62 ± 44 | 19 ± 9 | 14 ± 10 | 2 ± 1* | 12 ± 9 |
| Apoptotic | 19 ± 14 | 21 ± 16 | 22 ± 9 | 30 ± 17 | 30 ± 28 | 45 ± 32 |
| | | | Body weight loss, % of pretreatment level | | | |
| | 1% | 5% | 13% | 0% | 0% | >20%** |

*p < 0.05 compared to all other groups.
**p < 0.05 compared to control, paclitaxel alone and paclitaxel plus low suramin groups.

In addition, the effect of the foregoing treatment methods on body weight was determined. These results are shown in Table 1. Compared to animals treated with saline, animals treated with low dose suramin alone, paclitaxel alone or the paclitaxel/low dose suramin combination did not show body weight loss (p>0.05), whereas animals treated with high dose suramin alone or the paclitaxel/high dose suramin combination showed significant weight loss (p<0.05). This data indicates that high dose suramin produced host toxicity, whereas low dose suramin did not produce measurable toxicity.

Pharmacokinetic studies were conducted to determine the plasma concentrations of suramin and paclitaxel. For paclitaxel, the plasma concentrations declined from about 7 μg/ml at 5 minutes after injection to 0.2 μg/ml at 5 hours, and were not measurable (i.e., less than 0.1 μg/ml) at 6 hours. Hence, nearly all of the paclitaxel exposure occurred in five hours. Administration of the first dose of the low dose suramin regimen yielded plasma concentrations of between about 15 to about 50 μM for 8 hours. Administration of the first dose of the high dose suramin regimen (i.e., 200 mg/kg) yielded plasma concentrations of between about 300 to about 650 μM in the first six hours. Administration of the first and second doses of the high dose suramin regimen (i.e., 200 and 130 mg/kg, respectively) yielded plasma concentrations of between about 100 to 650 μM over 48 hours.

A comparison of the plasma concentration-time profiles of paclitaxel and of suramin after the low and high dose regimens, together with the chemosensitization observed for the low dose suramin regimen and the lack of chemosensitization observed for the high dose suramin regimen, indicate the following: (a) suramin produced chemosensitization at low doses that produced plasma concentrations of between about 15 to about 50 μM over 8 hours, or approximately the same duration when paclitaxel was present at therapeutically significant levels, and (b) suramin did not produce chemosensitization at high doses that produced high plasma concentrations of between about 300 to about 650 μM for 6 hours or approximately the same duration when paclitaxel was present at therapeutically significant levels.

Collectively, these results indicate that suramin, at low doses, significantly enhanced the antitumor activity of paclitaxel, without enhancing the host toxicity. In contrast, high dose suramin did not significantly improve the activity of paclitaxel, but significantly enhanced host toxicity. These results further show that the chemosensitizing effect of suramin requires the presence of suramin at chemosensitizing concentrations only during the time when the other chemotherapeutic agent is present at therapeutically significant levels.

Example II

Low Dose Suramin Improves the Response of Lung Cancer Patients to Chemotherapy

A Phase I trial was performed in advanced non-small lung cancer patients. One of the objectives was to determine whether low dose suramin is effective in enhancing the efficacy of chemotherapy. Suramin at doses that delivered plasma concentrations of between about 10 to about 50 μM for 48 hours was administered with a standard therapy, i.e., paclitaxel (200 mg/m$^2$) and carboplatin (AUC 6), every three weeks. Fifteen patients, with metastases to pleura, pericardium, adrenals, lymph nodes, liver, bone, and/or brain, were enrolled in the phase I trial. This group includes 4 stage IIIb and 11 stage IV patients. Seven patients had received prior chemotherapy (paclitaxel, vinorelbine and/or platinum) and radiation. All patients were evaluable for pharmacokinetics and toxicity. No dose-limiting toxicity was observed. Furthermore, no adrenal insufficiency, which is a common toxicity in patients receiving high dose suramin treatment (Dorr and Von Hoff), was not observed in patients receiving the low dose suramin treatment. Accordingly, it was not necessary to administer replacement steroid therapy to patients who received low dose suramin. This is contrary to the case where replacement steroid therapy was routinely given to patients who received high dose suramin (Dorr and Von Hoff).

The fifteen enrolled patients received a total of 85 treatments. Three patients were taken off protocol within the first two days or after the first treatment (one due to a reaction to paclitaxel, one due to the need for radiation to a spinal cord metastasis, and one because she was found to have small cell lung cancer instead of nonsmall cell lung cancer). The remaining 12 patients received a total of 82 courses (range of 4-10 courses, median of 6 courses).

Of the 12 patients who received more than one treatment, two had only malignant pleural involvement and no measurable lesions. The response rate in the remaining ten patients who had measurable disease is 60%, based on the RECIST criteria established by the National Cancer Institute.

Table 2 compares the results in patients who received low dose suramin plus paclitaxel and carboplatin to the historical results in patients with comparable diseases and who received only paclitaxel and carboplatin (Laohavinij, et al. *Lung Cancer*, 26:175-185, 1999; Helsing, et al., *Lung Cancer*, 24:107-113, 1999; Langer, et al. *Eur. J. Cancer*, 36:183-193, 2000; Evans, et al. *Lung Cancer*, 18:83-94, 1997; Langer et al. *J. Clin. Oncol.*, 13:1860-1870, 1995).

TABLE 2

Effect of Suramin On Chemotherapy Efficacy In Patients

| Treatment | Response rate | Median time to disease progression (months) | One year survival rate | Median survival time (months) |
|---|---|---|---|---|
| Suramin + paclitaxel + carboplatin | 60% | 8.5 | 67% | >17 |
| Paclitaxel + carboplatin (historical results) | 30% | 4 to 5 | 40% | 8 to 10 |

Hence, the clinical results of the phase I study suggest a therapeutic advantage of using low dose suramin as a chemosensitizer, and provide the preliminary proof-of-concept that suramin, at nontoxic doses and concentrations, enhances the efficacy of chemotherapy in cancer patients.

This finding is surprising in view of the prior art, in two respects. The beneficial effect of suramin found in the present study is opposite to the prior art teaching that suramin does not improve the efficacy of other cytotoxic agents (Falcone, 1998; Falcone, 1999; Miglietta, 1997; Rapaport, 1993). These earlier trials used high dose suramin that produced constant plasma concentrations of between about 100 to 200 µM maintained for more than one or two months. The finding that low dose suramin provided beneficial effects, whereas these earlier trials did not find beneficial effects for high dose suramin, is consistent with the results shown in Example I, but is surprising because these observations are opposite to the generally accepted pharmacological principle that higher drug levels produce higher rather than lower effect.

Example III

Pharmacokinetics of Low Dose Suramin in Lung Cancer Patients

One of the objectives of the phase I trial described in Example II was to identify the suramin dose yielding target plasma concentrations of between about 10 to about 50 µM over the duration when the chemotherapeutic agents, i.e., paclitaxel and carboplatin, were present at therapeutically significant levels in the plasma.

Patients were given, sequentially, infusions of suramin, paclitaxel (initial dose of 175 mg/m$^2$, escalating to 200 mg/m$^2$ after establishing the suramin dose) and carboplatin (area-under-concentration-time-curve or AUC of 6 mg/min/ml), every 3 weeks.

The unusually long half-life of suramin resulted in residual plasma concentrations at the time of subsequent treatments, given 3 weeks later. Hence, real time pharmacokinetics, based on the residual suramin concentrations detected at 72 hours prior to subsequent dosing, was used to determine the dose of subsequent treatments in the first 12 patients. The pharmacokinetic data obtained from these 12 patients were then used to develop a method to calculate the target suramin dose based on several parameters, i.e., target suramin concentrations, squared value of patient body surface area, gender, and time lapsed since last suramin treatment. This method was then verified prospectively in three additional patients (see Example IV).

Results in the first six patients showed that nearly all of the areas-under-plasma concentration-time curves of paclitaxel and carboplatin were attained in the first 48 hours after drug administration (i.e., >92% for paclitaxel and >99% for carboplatin). Hence, the target suramin concentrations were between about 10 to about 50 µM over 48 hours following the initiation of suramin infusion. These concentrations were achieved by giving the total suramin dose in two split doses, with two-thirds of the dose given on the first day and the remaining one-third given 24 hours later. This schedule was found to yield the target concentration range of less than 50 µM suramin concentrations immediately after the administration of a chemotherapeutic agent, i.e., paclitaxel, and greater than 10 µM suramin concentrations at 48 hours after the initiation of suramin infusion.

Table 3 compares the pharmacokinetic parameters of the low dose suramin regimen used in the present study with the literature values obtained using a >8-fold higher total suramin dose (Jodrell Example et al, *J Clin Oncol* 12:166-75, 1994). The comparison shows three unexpected findings. First, low dose suramin shows a much faster elimination compared to high dose suramin, as indicated by the higher clearance and shorter terminal half-life of the low dose. Second, low dose suramin shows a significantly lower steady state volume of distribution compared to high dose suramin. Third, suramin is eliminated more slowly in female patients compared to male patients. These findings are surprising because the elimination of suramin was not known to be dose-dependent or gender dependent.

TABLE 3

Pharmacokinetic Parameters Of Suramin**

| Pharmacokinetic Parameters | Literature | Current Overall | Current Male | Current Female |
|---|---|---|---|---|
| Total dose, mg per m$^2$ | >2,000 | 240 | 240 | 240 |
| Cumulative AUC, mg-hr/ml | 101* | 10.2 ± 2.3 | 9.3 ± 1.3 | 12.9 ± 2.7 |
| Alpha half-life, hr | 5.5 ± 1.7 | 4.4 ± 1.1 | 4.3 ± 0.6 | 4.6 ± 2 |
| Beta half-life, day | 4.1 ± 2.2 | 11 ± 3 | 10 ± 1.9 | 14 ± 3.8 |
| Gamma half-life, day | 78 ± 46 | Not applicable | Not applicable | Not applicable |
| V1, liter per m$^2$ | 2.7 ± 0.5 | 1.8 ± 0.2 | 1.8 ± 0.2 | 1.7 ± 0.3 |
| V2, liter per m$^2$ | 4.2 ± 1.4 | 6.7 ± 1.2 | 6.8 ± 1.3 | 6.4 ± 0.5 |
| V3, liter per m$^2$ | 12.5 ± 3.9 | Not applicable | Not applicable | Not applicable |
| Vdss⊥ | 23.6‡ | 8.5 ± 1.2‡ | 8.6 ± 1.3 | 8.2 ± 0.6 |

TABLE 3-continued

Pharmacokinetic Parameters Of Suramin**

| Pharmacokinetic Parameters | Literature | Current | | |
|---|---|---|---|---|
| | | Overall | Male | Female |
| Total body clearance (l/hr/m²) | 0.01 ± 0.004§ | 0.025 ± 0.005§ | 0.026 ± 0.0042 | 0.017 ± 0.0042 |

*AUC was calculated as (average steady state concentration, 200 µg/ml) multiplied by (time, 3 weeks) from the data provided in the reference (Jordell et al).
⊥Vdss was estimated as the product of mean residence time and clearance.
‡, §2: P < 0.05, unpaired two tailed Student's t-test.
**Comparison of pharmacokinetics of low dose suramin used as a chemosensitizer to pharmacokinetics of high dose suramin used as a cytotoxic agent. As the pharmacokinetics of low dose suramin was adequately described by a two-compartment model, values for the gamma half-life and V3 are not applicable. Because the current study administered suramin every 3 weeks whereas earlier studies administered suramin at more frequent intervals, the dose and AUC were normalized per 3-week interval. AUC is the area-under-plasma concentration-time curve. V is volume distribution Example IV Methods for Identifying an Effective Suramin Dose for Use in Combination with Other Chemotherapeutic Agents As shown in Example I, the ability of suramin to improve the chemotherapy efficacy in tumor-bearing animals is highly dependent on the suramin concentration. This is further supported by the surprising finding that low dose suramin enhanced the efficacy of chemotherapy in human lung cancer patients, as shown in Example II. The surprising findings of dose- and gender-dependent elimination of suramin, shown in Example III, highlight the importance to determine the dose of suramin that would yield plasma concentrations that are known to produce chemosensitization. Similarly, it is necessary to identify the high doses of suramin that do not produce chemosensitization but only potentiate the toxicity of other chemotherapeutic agents.

The objective of this example is to demonstrate the development of a method to identify the sources of the inter-subject variability in the suramin pharmacokinetics in patients and to use this information to identify, for individual patients, the dose of suramin that would produce chemosensitization. This was accomplished by using population-based pharmacokinetic analysis (PBPK) of the mathematical relationships between suramin pharmacokinetic parameters and clinical covariates obtained in the first 12 patients. These mathematical relationships were then used to develop empirical equations that predict suramin dose based on several parameters. Finally, the predictive performance of this equation was verified in 3 additional patients.

Inter-Subject Variability in Suramin Pharmacokinetics

Analysis of the suramin plasma concentration-time data by standard methods indicated that although the disposition of suramin was consistent with a 2-compartment model (respective initial and terminal half-lives were 4.4 hr, and 11 days), the area under the terminal phase accounted for most of the total area-under-curve (i.e., ~90%). Hence, PBPK analysis can be conducted using a one-compartment pharmacokinetic model and using the data points obtained during the terminal phase (e.g., 18 hours or later, or greater than 4 times the half-life of the initial phase).

Table 4 summarizes the suramin pharmacokinetic parameters of the first 12 patients. The clearance (CL) of suramin showed relative low inter-individual variability within each gender, with 13% variability in males and 2% variability in females. However, the CL was lower in females compared to males. This, in turn, resulted in a maximum inter-individual variability of 182%. The maximum inter-subject variability in the steady state volume of distribution (Vss) was 153%.

TABLE 4

Variability Of Pharmacokinetics Of Low Dose Suramin

| | Clearance (mL/hr/m2) | | | Vss (mL/m²) | | |
|---|---|---|---|---|---|---|
| | Range | Mean | SD | Range | Mean | SD |
| Overall | 16.4-29.8 | 24.1 | 4.8 | 6.8-10.4 | 8.5 | 1.2 |
| Males | 23.0-29.8 | 25.9 | 3.3 | 7.5-8.8 | 8.2 | 0.6 |
| Females | 16.4-16.8 | 16.6 | 0.4 | 6.8-10.4 | 8.6 | 1.3 |

PBPK Analysis

The pharmacokinetic data of low dose suramin was analyzed using a nonlinear mixed-effects model (NONMEM Version V, UCSF, San Francisco, Calif.). PBPK analysis is used to identify the sources of inter-individual variability in pharmacokinetic parameters and is performed in a stepwise manner (Sheiner, et al., *J. Pharmacokinet. Biopharm.*, 5: 445, 1977; Mandema, et al, *J. Pharmacokinet. Biopharm.*, 20: 511, 1992).

The first step is to define the appropriate error model for the pharmacokinetic parameters of interest. Second, the physiological or pathological parameters of patients (referred to as covariates) that significantly reduce the deviation of the values in individual patients from the population mean values are incorporated into the model (referred to as the Full Model). Third, to ascertain that the selected covariates are the critical determinants of inter-individual variability and to eliminate redundant covariates (e.g., covariates that are highly correlated with each other but do not contribute to the variability), a backward elimination procedure is performed by determining whether eliminating individual covariates affects the performance of the Full Model. Only the covariates whose elimination results in significant deterioration in model performance are included in the final model (referred to as Population Model). These steps are detailed below.

Model Building: Basic Model $$C_{ij} = \frac{Dose}{V_j} e^{-\frac{CL_j}{V_j} time_i} \quad \text{Eq. 1}$$

The PBPK for a one-compartment model depicting plasma concentrations as a function of clearance (CL) and volume of distribution (V) is as follows:
where $C_{ij}$ is the predicted plasma concentration at a particular time time i for a patient j.

Error functions were used to describe the random deviations between model-predicted and observed data for individual pharmacokinetic parameters. Because the objective was to identify the dose, which can be calculated based on CL and V, the analysis focused on these two parameters. Equations 2 and 3 describe the deviation of CL ($CL_j$) and V ($V_j$) in an individual patient from the population or typical values ($CL_{typ}$ and $V_{typ}$).

$$CL_j = CL_{typ} * (1 + \eta_{CL}) \quad \text{Eq. 2}$$

$$V_j = V_{typ} * (1 + \eta_V) \quad \text{Eq. 3}$$

where $\eta_{CL}$ and $\eta_V$ are random values normally distributed around a mean of zero with a variance of $\omega^2$.

Multiple plasma concentration-time data points were used in PBPK analysis. These time points were 18, 24, 48 and 72 hours after the first treatment, 72 hours and immediately prior to next treatment, and 48 and 72 hours after second and subsequent treatments. The relationship between observed plasma concentrations and PBPK-predicted values (residual variability) is depicted by Equation 4.

$$Y_{ij} = C_{ij} * (1 + \epsilon_{1ij}) \quad \text{Eq. 4}$$

where $Y_{ij}$ and $C_{ij}$ are the observed and predicted concentrations of the $j^{th}$ individual at the $i^{th}$ sampling time. $\epsilon_{1ij}$ is the residual errors with a mean of zero and a variance of $\sigma^2$. The above equations used an error function in the form of (1+error), which represents the proportional error model where the coefficient of variation is constant and independent of the size of the fixed effect parameter. A comparison of this and other error models (i.e., addictive error model, and power model) using the objective function value, which indicates the goodness of fit as calculated by NONMEM, indicated that the proportional error model was the best in describing the inter-individual variability in CL and V in our patient population.

Model Building: Identification of Significant Covariates

The contribution of ten covariates to the inter-individual variability in CL and V was studied. These covariates were age, gender, weight, ideal body weight, height, body surface area (BSA), creatinine concentration, creatinine clearance (CrCL), and serum albumin concentration. Linear regression analysis was used to examine the relationships between covariates and pharmacokinetic parameters in individual patients. Covariates that showed a coefficient of determination of greater than 0.4 ($r^2 > 0.4$) were selected for further evaluation and were incorporated in the models for CL and V.

As an example, Equation 5 shows the relationship between $CL_{typ}$ (the mean value of population clearance) and creatinine clearance, and Equation 6 shows the relationship between $V_{typ}$ (the mean value of population volume of distribution) and BSA. Similar equations were established for other covariates.

$$CL_{typ} = \theta_1 + \theta_2 * CrCL \quad \text{Eq. 5}$$

$$V_{typ} = \theta_3 + \theta_4 * BSA \quad \text{Eq. 6}$$

These regression models assumed a linear relationship between $CL_{typ}$ and CrCL, and between $V_{typ}$ and BSA, with proportionality constants $\theta_2$ and $\theta_4$ (referred to as fixed effect parameters). $\theta_1$ represents the value of $CL_{typ}$ that is not related to CrCL, $\theta_2$ represents the value of $CL_{typ}$ that is related to CrCL, $\theta_3$ represents the value of $V_{typ}$ that is not related to BSA, and $\theta_4$ represents the value of $V_{typ}$ that is related to BSA.

To determine whether a covariate should be incorporated into the model, the log likelihood ratio test was used and the chi-square $\chi^2$ values were calculated by taking the difference in the objective function values of the models, obtained with or without adding the candidate covariate. A reduction in the objective function values of more than 3.9 (i.e., $\chi^2$ value associated with P<0.05 for 1 degree of freedom or addition of single covariate) was required for inclusion into the Full Models for $CL_{typ}$ and $V_{typ}$.

The covariates that showed the highest correlations with $CL_{typ}$ were BSA, CrCL, and gender. The covariates that showed the highest correlations with $V_{typ}$ were body weight and $BSA^2$. The remaining covariates did not show significant correlations in the linear regression analysis, and did not significantly affect the model performance. The Full Models for $CL_{typ}$ and $V_{typ}$ were described by Equations 7 and 8, respectively.

$$CL_{typ} = (\theta_1 * BSA + \theta_2 * CrCL + \theta_3) * (1 - \theta_4) \quad \text{Eq. 7}$$

$$V_{typ} = \theta_5 * BSA^2 + \theta_6 \quad \text{Eq. 8}$$

$\theta_1$, $\theta_2$, and $\theta_4$ described the effects of BSA, CrCL, and gender on $CL_{typ}$, respectively. For males, $\theta_4$ was set to zero. For females, the value of $\theta_4$ was determined by data-fitting. $\theta_5$ is the proportionality constant that described the effect of ($BSA^2$) on $V_{typ}$ and $\theta_6$ describes the changes in $V_{typ}$ that was not accounted for by changes in BSA. Body weight, BSA, and $BSA^2$ were tested for inclusion into the Full Model for $V_{typ}$. $BSA^2$ was chosen because it produced the lowest objective function values.

Inclusion of additional covariates would, as a general rule, reduce the random error of the statistical model but increase the parameterization. To ascertain that the selected covariates played an important role in the model performance, the final model was obtained by removing insignificant covariates from the Full Model in a backward elimination process. In this process, a more restrictive criterion was used. To eliminate a parameter from the Full Model, a difference in the objective function of more than 7.9 was required ($\chi^2$ value associated with P<0.005 and 1 degree of freedom). Removal of each of the three, fixed effect parameters, i.e., $\theta_2$, $\theta_3$, and $\theta_6$, either individually or simultaneously, from the Full Model altered the objective function value by less than that would required for inclusion. Hence, $\theta_2$, $\theta_3$, and $\theta_6$ were removed from the Full Model.

The remaining three significant parameters were $\theta_1$, $\theta_4$, and $\theta_5$. The final Population Model consisted of only the covariates that contributed significantly to inter-individual variability in CL and V, and described by Equations 9 and 10. The parameter estimates are shown in Table 5.

$$CL_{typ} = (\theta_1 * BSA) * (1 - \theta_4) \quad \text{Eq. 9}$$

$$V_{typ} = \theta_5 * BSA^2 \quad \text{Eq. 10}$$

TABLE 5

Estimates for Population Model Parameters

| Parameters | Estimate | CV, % | 95% Confidence interval |
|---|---|---|---|
| $\theta_1$ | 26.2 (mL/h * m$^2$) | 2.70% | 24.6-27.4 (ml/h * m$^2$) |
| $\theta_4$ | 0.31 | 7.90% | 0.26-0.36 |
| $\theta_5$ | 5.13 (L/m$^4$) | 4.40% | 4.49-5.57 (l/m$^4$) |
| k$_{typ}$, (Male) | 0.0026 (hr$^{-1}$) | 7.3% | 0.0023-0.0030 (hour$^{-1}$) |
| k$_{typ}$, (Female) | 0.0022 (hr$^{-1}$) | 4.7% | 0.0020-0.0024 (hour$^{-1}$) |

* The population pharmacokinetic parameters were obtained using data from the first 12 patients in the phase I study. Typical values for different fixed effect parameters ($\theta_1$, $\theta_4$, and $\theta_5$) and estimates of variability from CL and V are presented with the respective coefficients of variation (CV %).

Coefficient of variations (CV) and 95% confidence interval were generated based on the standard errors of the fixed effect parameter estimates. The Population Models using only two covariates, BSA and gender, reduced the estimated inter-individual variability in CL by 6-fold from 30% to 6%, and reduced the estimated inter-individual variability in V by >6.5-fold from 20% to 3%. The estimated residual variability ($\sigma_{\epsilon1}$) decreased slightly from 21% to 18%.

Derivation of Equation for Suramin Dose Calculation

A simplified version of Equation 1, followed by rearrangement yielded Equation 11.

$$\text{Dose} = \frac{Cp * V}{e^{-k*t}} \qquad \text{Eq. 11}$$

The elimination rate constant, (k), was described by Equation 12.

$$k_{typ} = \frac{CL_{typ}}{V_{typ}} \qquad \text{Eq. 12}$$

Substituting Equations 9 and 10 and the values of $\theta_1$, $\theta_4$, and $\theta_5$ into Equation 12 yields Equations 12 and 13.

$$\text{For Males, } k_{typ} = \frac{0.0051 \text{ m}^2\_\text{hr}^{-1}}{BSA} \qquad \text{Eq. 13}$$

$$\text{For Females, } k_{typ} = \frac{0.0035 \text{ m}^2\_\text{hr}^{-1}}{BSA} \qquad \text{Eq. 14}$$

To obtain estimates for $k_{typ}$, the k values for individual patients were calculated by substituting their corresponding BSA values into Equations 13 and 14. The $k_{typ}$ which represented the average k value was 0.0026 hour$^{-1}$ for males and 0.0022 hour$^{-1}$ for females. The variability within each gender was relatively low; the coefficient of variation was 7% for males and 5% for females. Hence, in order to simplify the equation for dose calculation, a constant value for k was used (i.e., 0.0026 hour$^{-1}$ for males and 0.0022 hour$^{-1}$ for females).

The following discussion is offered as an example to use Equation 11 to calculate the suramin dose that would yield the target concentration of 15 μM or 21.4 μg/ml at 48 hours. Substituting 21.4 μg/ml for Cp and 48 hours for t, the Population Model values for V and the numerical values of $k_{typ}$, into Equation 11 yielded Equation 15.

$$\text{First cycle dose\_mg\_} = \frac{21.4 * 5.13 * BSA^2}{e^{-\_0.0026 \text{ or } 0.0022*48\_}} \qquad \text{Eq. 15}$$
$$= FACTOR * BSA^2$$

The numerical values of FACTOR were calculated to be 125 mg/m$^4$ for males and 123 mg/m$^4$ for females. Because of the relatively small difference (i.e., <2%) in the FACTOR values for the two genders, and for the ease of dose calculation, the value of FACTOR was set at 125 mg/m$^4$ for both genders. A larger gender-related difference (e.g., >10%) would require different FACTOR values for the two genders.

Chemotherapy is usually given in multiple cycles, e.g., weekly or every three weeks. Suramin is eliminated from the body very slowly. The data in non-small lung cancer patients show a long plasma half-life for suramin (about 11 days). Hence, a considerable fraction of the previous dose remains in the body at the time of the second and subsequent treatments (i.e., day 8 in weekly treatment regime or day 22 on every 3 week treatment regime). As a result, the suramin dose for second and subsequent treatment cycles has to be adjusted for the residual suramin.

To attain the same target concentrations of 21.4 μg/ml at 48 hours during subsequent treatment cycles, the dose administered during a subsequent cycle should replace the fraction of the dose that was eliminated during the interval between treatments. This is described in Equation 16.

$$\text{Subsequent cycle dose} = \text{First dose}*(1-e^{-k*t})$$
$$= 125*BSA^2*(1-e^{-k*t}) \qquad \text{Eq. 16}$$

Note that in contrast to the first cycle where t equaled 48 hours, the value of t during subsequent cycles is a variable that equals the time lapsed since the previous cycle. Furthermore, the value of t for the subsequent cycles is significantly longer than the value of t for the first cycle (e.g., ≥504 vs. 48 hours). This results in a much greater difference in the values of the (k*t) products between males and females. Accordingly, calculations of doses for subsequent cycles required gender-based adjustment.

The finding that the suramin dose is a function of the squared value of body surface area is surprising because in clinical oncology, the dose of chemotherapeutic agents is usually selected or calculated based on the body surface area and not its squared value.

Validation Of PBPK-Based Dosing Method

The performance of the PBPK-based suramin dosing method was examined retrospectively and prospectively. The retrospective analysis was performed in the first 12 patients whose pharmacokinetic data were used for model development. The dose calculated using the PBPK-based method was compared to the dose, found by real time pharmacokinetic studies, which would have yielded 15 μM suramin in plasma at 48 hours (referred to as Ideal Dose) in individual patients. The Ideal Dose accounted for inter-individual variations in drug disposition and was calculated using Equation 17.

$$\text{Ideal Dose} = \frac{\text{admininistered dose}\_Cp_{48hr,target}}{Cp_{48hr,observed}} \qquad \text{Eq. 17}$$

Where $Cp_{48\ hr,\ target}$ is the target plasma concentration at 48 hours and equaled to 15 μM or 21.4 μg/ml. $C_{48\ hr,\ observed}$ is the concentration observed at 48 hours. Dose accuracy between the PBPK method-predicted dose and Ideal Dose was calculated using Equation 18.

$$\text{Dose accuracy, \%} = \frac{\text{Predicted dose}}{\text{Ideal Dose}}\_100 \qquad \text{Eq. 18}$$

As a group (i.e., all tested patients), the dose calculated by the PBPK method was 106±15% of the Ideal Dose. For individual patients, the dose calculated by the BSA method was 103±7% of the Ideal Dose. The good agreement between the model-predicted dose and the Ideal Dose indicates a good predictive power of the PBPK method.

The above discussion demonstrates how to obtain the target suramin concentration of about 15 μM at 48 hours. To obtain a maximum concentration of less than about 50 μM, e.g., immediately after administration of a chemotherapeutic agent, pharmacokinetic calculations were performed using standard methods and the pharmacokinetic parameters of low dose suramin described in Table 4 in Example III, e.g., by simulating the plasma concentration-time profiles. Results of pharmacokinetic analysis indicate that the first and subsequent cycle suramin doses calculated by Equations 15 and 16 would yield a maximum concentration that are between about 50 to about 100 μM. Additional pharmacokinetic analysis, e.g., by simulation, indicated two approaches to obtain the desired maximum concentration of about or below 50 μM while maintaining the 48-hour concentration at about 10 μM. One approach is to divide the total calculated suramin dose into two portions, the first portion equaling two-thirds (⅔) of the total dose given prior to chemotherapy, followed by the remaining one-third (⅓) of the dose given 24 hours later. The second approach is to give the total suramin dose all at once, wait for about 2 to about 4 hours, when the suramin concentration declines to about or below 50 μM, and then administer a chemotherapeutic agent.

To further verify whether the suramin dose calculated by the PBPK method can deliver between about 10 to about 50 μM plasma concentrations of suramin over 48 hours, a prospective analysis was performed on a subset of patients. Three additional non-small cell lung cancer patients were treated using the dose calculated by the PBPK-based method. Two-thirds of the total suramin dose was given prior to the administration of a chemotherapeutic agent, and the remaining one-third was given 24 hours later. The suramin plasma concentrations from these patients (total of 13 treatments) were used to evaluate the concentration accuracy by comparing the observed concentration to the target concentration (i.e., 15 μM) at 48 hour, as follows:

$$\text{Concentration accuracy, \%} = \frac{Cp_{48hr,observed} - Cp_{48hr,target}}{Cp_{48hr,target}} \_100 \qquad \text{Eq. 19}$$

Table 6 shows the results. The 48-hour plasma concentrations in all treatments were above 10 μM. Furthermore, the maximum concentrations after administration of another chemotherapeutic agent, i.e., paclitaxel, in all treatments were below 50 μM. The difference between the target and observed plasma concentrations of 15 μM at 48 hours were <17%.

The following discussion is offered as an example of nomogram development. For this example, the target suramin concentrations were 50 μM immediately after administration of another chemotherapeutic agent and 15 μM at 48 hours, and the k values were 0.0026 hour$^{-1}$ for males and 0.0022 hour$^{-1}$ for females.

Using these values, the numerical values of FACTOR were calculated to be 125 mg/m$^4$ for males and 123 mg/m$^4$ for females. Because of the relatively small difference (i.e., <2%) in the FACTOR values for the two genders, and for the ease of dose calculation, the value of FACTOR was set at 125 mg/m$^4$ for both genders. A larger gender-related difference (e.g., >10%) would require different FACTOR values for the two genders.

The value of FACTOR for subsequent cycle treatments depends on the time elapsed since the administration of the initiation of the suramin treatment during the previous cycle (see Table 7 below). It is noted that for the subsequent cycle dose, the difference between male and female patients is larger than for the loading dose. This is because the 20% difference in the k values for the two genders resulted in a much larger difference in the product of (k*time) when time t was increased from 48 hours to 504 hours Note that FACTOR is a function of the target concentration Cp, k value and t, which is the time when the target concentration is attained. Hence, FACTOR can be calculated based on the desired target concentration attained at the desired time t. For example, for the first cycle treatment, FACTOR can be calculated based on the desired Cp at time t and the k values. For subsequent cycle treatments, FACTOR for a weekly treatment schedule can be calculated using at value of 168 hours, and at value of 504 hours for an every-3-week treatment schedule. Likewise, the FACTOR can be calculated for different target concentrations, e.g., 10 or 20 μM.

The FACTOR can also be used to adjust for the variation in treatment time, e.g., delay in treatment due to the travel schedule of patients. For example, if the second cycle is initiated 25 days after the administration of the first dose during the previous first cycle, the value of the FACTOR is 87

TABLE 6

Prospective Verification of the PBPK Method

| Patient ID | Cycles number | Sex | BSA | Dose (mg) | Concentration (μM) | | |
|---|---|---|---|---|---|---|---|
| | | | | | Pre-dose | Post-paclitaxel | 48 hours |
| 1 | 1 | F | 1.45 | 263 | 0.00 | 33.95 | 13.93 |
| 1 | 3 to 6 | F | 1.44-1.47 | 151-156 | 1.87-3.19 | 21.5-26.3 | 10.2-11.5 |
| 2 | 1 | M | 1.67 | 210 | 0.00 | 40.39 | 15.53 |
| 2 | 2 to 6 | M | 1.68-1.70 | 227-257* | 2.65-3.81 | 26.7-28.5 | 12.9-15.6 |
| 3 | 1 | F | 1.83 | 230 | 0.00 | 36.02 | 19.40 |

*One of the doses was adjusted for the delay in dosing interval.

Nomogram For Calculating Suramin Dose

As shown in Equations 15 and 16, both the first and subsequent cycle doses can be calculated based on the target concentrations at target time points, and the squared value of body surface area and gender of the patient. Hence, a nomogram can be developed to calculate the target suramin dose. A nomogram facilitates the dose determination in a clinical setting, e.g., community medical offices.

for a man and 79 for a woman, whereas the values of FACTOR are 80 for a man and 72 for a woman who receive treatments every three weeks (i.e., 21 days after the administration of the first dose during the previous cycle). Likewise, for a weekly schedule, the amount of residual suramin is greater than that after an every-3-week schedule. Accordingly, the FACTOR values are smaller, at 39 for males and 33 for females.

TABLE 7

Sex-Based Nomogram For Calculating Suramin Dose

| Days since the administration of the first dose of previous cycle | Man Cycle 1* 125 FACTOR | Woman Cycle 1* 125 FACTOR |
|---|---|---|
| 7 | 39 | 33 |
| 8 | 43 | 37 |
| 9 | 47 | 40 |
| 10 | 51 | 44 |
| 11 | 55 | 47 |
| 12 | 58 | 50 |
| 13 | 61 | 53 |
| 14 | 64 | 56 |
| 15 | 67 | 58 |
| 16 | 70 | 61 |
| 17 | 72 | 63 |
| 18 | 74 | 66 |
| 19 | 77 | 68 |
| 20 | 79 | 70 |
| 21 | 80 | 72 |
| 22 | 82 | 74 |
| 23 | 84 | 75 |
| 24 | 86 | 77 |
| 25 | 87 | 79 |
| 26 | 88 | 80 |
| 27 | 90 | 82 |
| 28 | 91 | 83 |
| 29 | 92 | 84 |
| 30 | 93 | 86 |
| 31 | 94 | 87 |
| 32 | 95 | 88 |
| 33 | 96 | 89 |
| 34 | 97 | 90 |
| 35 | 98 | 91 |
| 36 | 98 | 92 |
| 37 | 99 | 93 |
| 38 | 100 | 94 |
| 39 | 100 | 95 |
| 41 | 102 | 96 |
| 42 | 102 | 97 |
| 44 | 103 | 98 |
| 47 | 104 | 100 |
| 49 | 105 | 101 |
| 52 | 106 | 102 |
| 55 | 106 | 103 |

*Subsequent cycles: Values of Factor depends on the elapsed time (in days) since the administration of the first dose of previous cycle, as provided in Table 7.

Should the practitioner desire to calculate the suramin dose without regard to sex bias, an efficacious treatment regimen in accordance with the precepts of the present invention still would be accorded the patient. The nomogram for such unisex treatment regimen is displayed below in Table 8.

TABLE 8

Unisex Nomogram For Calculating Suramin Dose

| Days since the administration of the first dose of previous cycle | Cycle 1* 125 FACTOR |
|---|---|
| 7 | 39 |
| 8 | 43 |
| 9 | 47 |
| 10 | 51 |
| 11 | 55 |
| 12 | 58 |
| 13 | 61 |
| 14 | 64 |
| 15 | 67 |
| 16 | 69 |
| 17 | 72 |
| 18 | 74 |
| 19 | 76 |
| 20 | 78 |
| 21 | 80 |
| 22 | 82 |
| 23 | 84 |
| 24 | 86 |
| 25 | 87 |
| 26 | 88 |
| 27 | 90 |
| 28 | 91 |
| 29 | 92 |
| 30 | 93 |
| 31 | 94 |
| 32 | 95 |
| 33 | 96 |
| 34 | 97 |
| 35 | 98 |
| 36 | 98 |
| 37 | 99 |
| 38 | 100 |
| 39 | 100 |
| 41 | 102 |
| 42 | 102 |
| 44 | 103 |
| 47 | 104 |
| 49 | 105 |
| 52 | 106 |
| 55 | 106 |

The methods described above use a target suramin concentration range of between 10 to 50 µM over 48 hours. This is specific for situations where the other chemotherapeutic agents to be used in combination with suramin have half-lives of less than 12 hours and, therefore, would be more than 90% eliminated in 48 hours. This same method for calculating the chemosensitization dose of suramin can be extended to other situations where the chemotherapeutic agents have longer half-lives. In this case, the target suramin concentrations will need to be maintained for at least four half-lives of the other chemotherapeutics. The suramin dose can be calculated from Equations 15 and 16, by substituting the time parameter, e.g., from 48 hours to the new target time (e.g., three to four times the terminal half-lives of the co-administered chemotherapeutic agent). The modified equations can then be used to calculate appropriate nomograms.

Summary

In summary, this Example, together with the results of Examples I through III, have demonstrated an approach to use PBPK analysis and a method to determine or calculate the suramin dose that produces chemosensitization in animals and in humans. The suramin dose calculated using this method would yield the desired target plasma concentrations over the duration when other chemotherapeutic agents are present in the plasma at therapeutically significant levels. In addition, the suramin dose calculated using this method would not yield plasma concentrations that do not produce chemosensitization. Finally, the use of PBPK analysis to determine the suramin dose that produces chemosensitization can be expanded to evaluate other patient characteristics, including, but not limited to, race, pre-adulthood vs. adulthood. The same method can also be applied to nonhuman patients.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application, all citations referred herein are expressly incorporated herein by reference.

We claim:

1. A method for determining a therapeutically effective amount of suramin for administering to a patient, who is to receive a cytotoxic agent, which comprises the steps of:
   (a) determining the gender and the squared value of the body surface area (BSA) of said patient;
   (b) determining the time elapsed, in days, since the initiation of the last suramin treatment; and
   (c) calculating the dose of low dose suramin using a nomogram that shows the dose according to the parameters of gender, squared value of body surface area, and elapsed days since last suramin treatment, wherein said nomogram comprises:

Nomogram for Calculating Suramin Dose

| Days elapsed since the initiation of the last suramin treatment | Cycle 1* FACTOR | |
|---|---|---|
| | Man 125 FACTOR | Woman 125 FACTOR |
| 7 | 39 | 33 |
| 8 | 43 | 37 |
| 9 | 47 | 40 |
| 10 | 51 | 44 |
| 11 | 55 | 47 |
| 12 | 58 | 50 |
| 13 | 61 | 53 |
| 14 | 64 | 56 |
| 15 | 67 | 58 |
| 16 | 70 | 61 |
| 17 | 72 | 63 |
| 18 | 74 | 66 |
| 19 | 77 | 68 |
| 20 | 79 | 70 |
| 21 | 80 | 72 |
| 22 | 82 | 74 |
| 23 | 84 | 75 |
| 24 | 86 | 77 |
| 25 | 87 | 79 |
| 26 | 88 | 80 |
| 27 | 90 | 82 |
| 28 | 91 | 83 |
| 29 | 92 | 84 |
| 30 | 93 | 86 |
| 31 | 94 | 87 |
| 32 | 95 | 88 |
| 33 | 96 | 89 |
| 34 | 97 | 90 |
| 35 | 98 | 91 |
| 36 | 98 | 92 |
| 37 | 99 | 93 |
| 38 | 100 | 94 |
| 39 | 100 | 95 |
| 41 | 102 | 96 |
| 42 | 102 | 97 |
| 44 | 103 | 98 |
| 47 | 104 | 100 |
| 49 | 105 | 101 |
| 52 | 106 | 102 |
| 55 | 106 | 103 | where:
Dose (mg)=FACTOR*BSA$^2$
wherein
"BSA" is body surface area in units of m$^2$.

2. A method for determining a therapeutically effective amount of suramin for administering to a patient, who is to receive a cytotoxic agent, which comprises the steps of:
   (a) determining the squared value of the body surface area (BSA) of said patient;
   (b) determining the time elapsed, in days, since the initiation of the last suramin treatment; and
   (c) calculating the dose of low dose suramin using a nomogram that shows the dose according to the parameters of squared value of body surface area, and elapsed days since last suramin treatment, and where said nomogram comprises:

Nomogram for Calculating Suramin Dose

| Days elapsed since the initiation of the last suramin treatment | Cycle 1* 125 FACTOR |
|---|---|
| 7 | 39 |
| 8 | 43 |
| 9 | 47 |
| 10 | 51 |
| 11 | 55 |
| 12 | 58 |
| 13 | 61 |
| 14 | 64 |
| 15 | 67 |
| 16 | 69 |
| 17 | 72 |
| 18 | 74 |
| 19 | 76 |
| 20 | 78 |
| 21 | 80 |
| 22 | 82 |
| 23 | 84 |
| 24 | 86 |
| 25 | 87 |
| 26 | 88 |
| 27 | 90 |
| 28 | 91 |
| 29 | 92 |
| 30 | 93 |
| 31 | 94 |
| 32 | 95 |
| 33 | 96 |
| 34 | 97 |
| 35 | 98 |
| 36 | 98 |
| 37 | 99 |
| 38 | 100 |
| 39 | 100 |
| 41 | 102 |
| 42 | 102 |
| 44 | 103 |
| 47 | 104 |
| 49 | 105 |

-continued

| Nomogram for Calculating Suramin Dose | |
|---|---|
| Days elapsed since the initiation of the last suramin treatment | Cycle 1*<br>125<br>FACTOR |
| 52 | 106 |
| 55 | 106 | where:
Dose (mg)=FACTOR*BSA$^2$
 wherein
  "BSA" is body surface area in units of m$^2$.

3. The method of claim 2, wherein said cytotoxic agent is one or more of an anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes one or more of apoptosis or necrosis, an interferon, an interleukin, a tumor necrosis factor, or radiation.

4. The method of claim 3, wherein said cytotoxic agent is one or more of paclitaxel, vincristine, vinblastine, vindesine, vinorelbin, docetaxel, topotecan, camptothecin, irinotecan hydrochloride, doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytosine arabinoside, trimetrexate, gemcitabine, acivicin, alanosine, pyrazofurin, N-phosphoracetyl-L-aspartate (PALA), pentostatin, 5-azacitidine, 5-aza-2'-deoxycytidine, adenosine arabinoside, cladribine, ftorafur, uracil/ftorafur combinations, 5-fluoro-2'-deoxyuridine, 5'-deoxy-5-fluorouridine, tiazofurin, capecitabine, cisplatin, carboplatin, oxaliplatin, mitomycin C, BCNU, melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycins, cytochalasins, depsipeptide, leuprolide, ketoconazole, tamoxifen, goserelin, flutamide, 4'-cyano-3-(4-fluorophenylsulphonyl)-2-hydroxy-2-methyl-3'-(trifluoromethyl) propionanilide, trastuzumab, anti-CD20, cetuximab, gefitinib, interferon alpha, interferon beta, interferon gamma, interleukin 2, interleukin 4, interleukin 12, tumor necrosis factors, radiation, hydroxyurea, azathioprine, aminopterin, trimethoprin, pyrimethamine, pyritrexim, DDMP (2,4 diamino- 5(3', 4' dichlorophenyl)6 methylpyrimidine), 5,10-dideazatetrahydrofolate, 10-propargyl-5,8 dideazafolate, 10-ethyl-10-deaza-aminopterin, deoxycytidine, 5-aza-cytosine arabinoside, N-4-palmitoyl-ara C, 2'-azido-2'-deoxy-ara C, N4-behenoyl-ara C, CCNU, estramustine, MeCCNU, triethylene melamine, trenimon, dimethyl busulfan, streptozotocin, chlorozotocin, procarbazine, hexamethylmelamine, pentamethylmelamine, tetraplatin, oxaliplatin, platinum-DACH, aziridinylbenzoquinone, bleomycin, tallysomycin S$_{10}$$^b$, liblomycin, pepleomycin, asparaginase, pegaspargase, leustatin, porfimer sodium, amonofide, deoxyspergualin, dihydrolenperone, flavone acetic acid, gallium nitrate, or hexamethylene bisacetamine.

5. A method for treating a patient with suramin for administering to a patient, who is to receive a cytotoxic agent, which comprises the steps of:
 (a) determining a therapeutically effective amount of suramin for administering to said patient, which comprises the steps of:
  (a1) determining the squared value of the body surface area (BSA) of said patient;
  (a2) determining the time elapsed, in days, since the initiation of the last suramin treatment; and
  (a3) calculating the dose of low dose suramin using a nomogram that shows the dose according to the parameters of squared value of body surface area, and elapsed days since last suramin treatment,
 wherein said nomogram comprises:

| Nomogram for Calculating Suramin Dose | |
|---|---|
| Days elapsed since the initiation of the last suramin treatment | Cycle 1<br>125<br>FACTOR |
| 7 | 39 |
| 8 | 43 |
| 9 | 47 |
| 10 | 51 |
| 11 | 55 |
| 12 | 58 |
| 13 | 61 |
| 14 | 64 |
| 15 | 67 |
| 16 | 69 |
| 17 | 72 |
| 18 | 74 |
| 19 | 76 |
| 20 | 78 |
| 21 | 80 |
| 22 | 82 |
| 23 | 84 |
| 24 | 86 |
| 25 | 87 |
| 26 | 88 |
| 27 | 90 |
| 28 | 91 |
| 29 | 92 |
| 30 | 93 |
| 31 | 94 |
| 32 | 95 |
| 33 | 96 |
| 34 | 97 |
| 35 | 98 |
| 36 | 98 |
| 37 | 99 |
| 38 | 100 |
| 39 | 100 |
| 41 | 102 |
| 42 | 102 |
| 44 | 103 |
| 47 | 104 |
| 49 | 105 |
| 52 | 106 |
| 55 | 106 | where: Dose (mg) =FACTOR*BSA$^2$
 wherein "BSA" is body surface area in units of m$^2$;
 (b) administering said calculated dose of suramin to said patient; and
 (c) administering said cytotoxic agent to said patient.

6. The method of claim 5, wherein a suramin dose is administered such that a concentration of between about 10 μM to about 50 μM between about 4 hours and about 48 hours after suramin administration is achieved in a patient.

7. The method of claim 5, wherein the patient is a mammal.

8. The method of claim 7, wherein the patient is a human.

9. The method of claim 5, wherein the patient has a tumor.

10. The method of claim 5, wherein the cytotoxic agent is one or more of carboplatin or paclitaxel.

11. The method of claim 5, wherein two-thirds of the therapeutically effective amount of suramin is given on the first day and the remaining one-third of the therapeutically effective amount of suramin is given about 24 hours later.

12. A method for treating a patient with suramin for administering to a patient, who is to receive a cytotoxic agent, which comprises the steps of:
 (a) determining a therapeutically effective amount of suramin for administering to said patient, which comprises the steps of:
  (a1) determining the gender and the squared value of the body surface area (BSA) of said patient;
  (a2) determining the time elapsed, in days, since the initiation of the last suramin treatment; and
  (a3) calculating the dose of low dose suramin using a nomogram that shows the dose according to the parameters of gender, squared value of body surface area, and elapsed days since last suramin treatment, wherein said nomogram comprises:

Nomogram for Calculating Suramin Dose

| Days elapsed since the initiation of the last suramin treatment | Cycle 1 FACTOR | |
|---|---|---|
| | Man 125 | Woman 125 |
| | FACTOR | |
| 7 | 39 | 33 |
| 8 | 43 | 37 |
| 9 | 47 | 40 |
| 10 | 51 | 44 |
| 11 | 55 | 47 |
| 12 | 58 | 50 |
| 13 | 61 | 53 |
| 14 | 64 | 56 |
| 15 | 67 | 58 |
| 16 | 70 | 61 |
| 17 | 72 | 63 |
| 18 | 74 | 66 |
| 19 | 77 | 68 |
| 20 | 79 | 70 |
| 21 | 80 | 72 |
| 22 | 82 | 74 |
| 23 | 84 | 75 |
| 24 | 86 | 77 |
| 25 | 87 | 79 |
| 26 | 88 | 80 |
| 27 | 90 | 82 |
| 28 | 91 | 83 |
| 29 | 92 | 84 |
| 30 | 93 | 86 |
| 31 | 94 | 87 |
| 32 | 95 | 88 |
| 33 | 96 | 89 |
| 34 | 97 | 90 |
| 35 | 98 | 91 |
| 36 | 98 | 92 |
| 37 | 99 | 93 |
| 38 | 100 | 94 |
| 39 | 100 | 95 |
| 41 | 102 | 96 |
| 42 | 102 | 97 |
| 44 | 103 | 98 |
| 47 | 104 | 100 |
| 49 | 105 | 101 |
| 52 | 106 | 102 |
| 55 | 106 | 103 | where: Dose (mg) = FACTOR*$BSA^2$
wherein "BSA" is body surface area in units of $m^2$;
 (b) administering said calculated dose of suramin to said patient; and
 (c) administering said cytotoxic agent to said patient.

13. The method of claim 12, wherein a suramin dose is administered such that a concentration of between about 10 μM to about 50 μM between about 4 hours and about 48 hours after suramin administration is achieved in a patient.

14. The method of claim 12, wherein the patient is a mammal.

15. The method of claim 14, wherein the patient is a human.

16. The method of claim 12, wherein the patient has a tumor.

17. The method of claim 12, wherein the cytotoxic agent is one or more of carboplatin or paclitaxel.

18. The method of claim 12, wherein two-thirds of the therapeutically effective amount of suramin is given on the first day and the remaining one-third of the therapeutically effective amount of suramin is given about 24 hours later.

* * * * *